June 3, 1958 T. E. MOTOSE Plant Pat. 1,715
ROSE PLANT
Filed Sept. 26, 1957
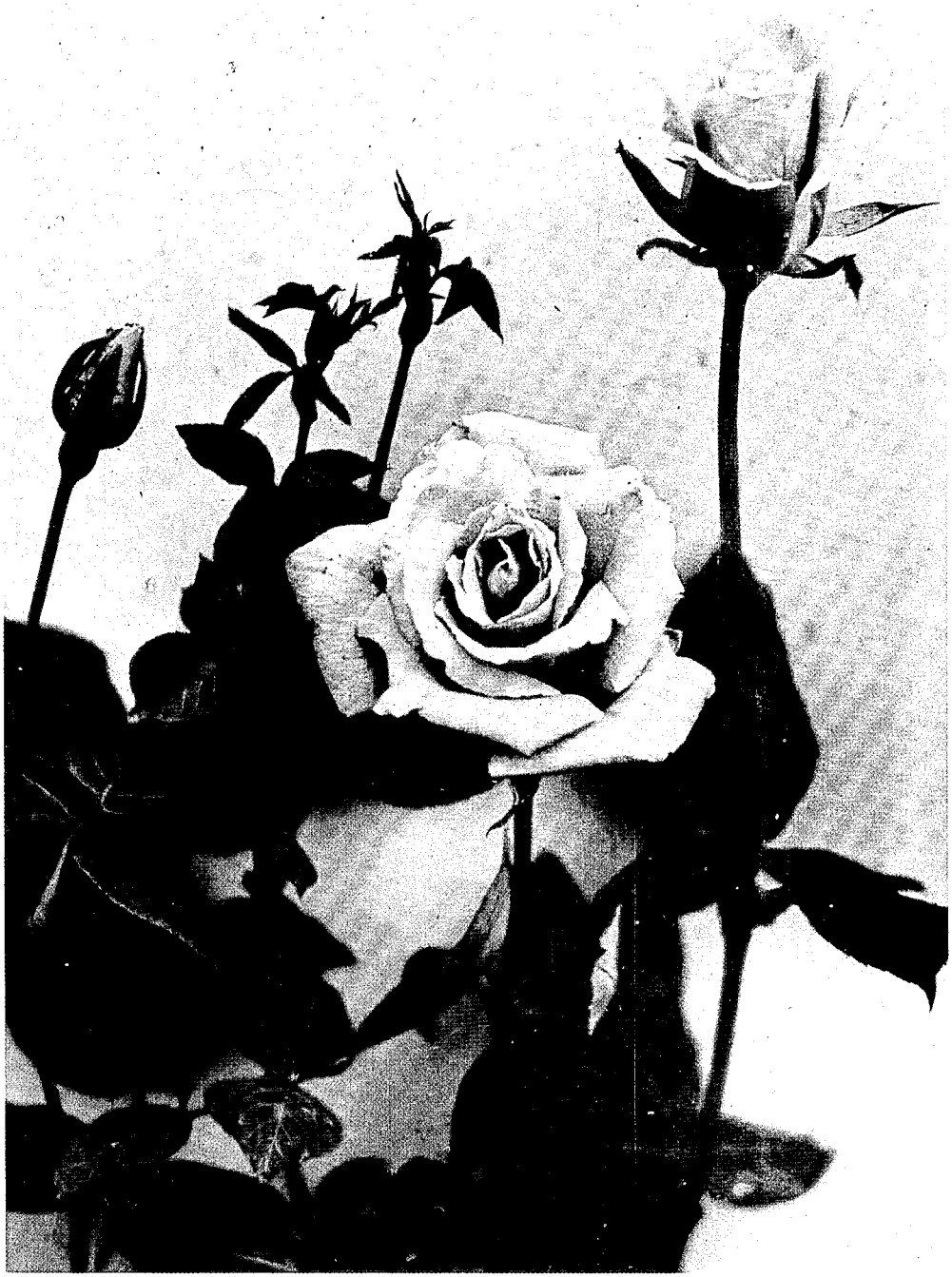
Inventor: Thomas Edison Motose United States Patent Office Plant Pat. 1,715
Patented June 3, 1958

1,715

ROSE PLANT

Thomas Edison Motose, Fairport, N. Y., assignor to George B. Hart, Inc., a corporation of New York Application September 26, 1957, Serial No. 686,549

1 Claim. (Cl. 47—61)

This invention relates to a new and distinct variety of rose plant, originating as a cross of an unnamed pink colored sport (mutant) of the known hybrid tea variety "Vierlanden" (not patented) and an unnamed seedling which was a cross between the known variety "Senator" (hybrid tea, not patented) and another known variety "Florex" (hybrid tea, not patented).

In making the crosses, I had for my object the origination of a new variety of rose plant adaptable for greenhouse or glass-house growing and capable of producing a large quantity of blooms of the type and quality suitable for the florists' or cut-flower trade. After numerous trials, the said objective was attained in the cross mentioned hereinbefore and to be described in detail hereinafter.

The named progenitors of this new variety are recognized in the horticultural world as distinct varieties, each with characteristics peculiar to itself and at the same time possessing certain characteristics in common. These strains have not been crossed successfully in the past in the said proportion or combination, and no other offspring of the same union or combination, possessing characteristics identical to those of this new variety, exists.

DIFFERENTIATING CHARACTERISTICS

This new variety possesses the following characteristics, which, when taken as a combination, make it different from all its parents, relatives and all other varieties of roses:

(*a*) Larger and longer canes or branches than those of its parents and the latters' parents;

(*b*) Tendency to produce a larger number of lateral canes or branches than its parents;

(*c*) Narrower and more pointed leaflets than those of its parents and the latters' parents;

(*d*) Decidedly less thorns than its parents and other progenitors, with practically no thorns on the upper half of the bush;

(*e*) Lighter and clearer pink coloring of its bloom as compared to those of its parents and progenitors;

(*f*) The bottom and lower section of its partly open bloom resembling the form or line drawn by the capital letter U;

(*g*) Slow unfurlment of its petals with a tendency of the bloom to remain in the very desirable partly opened stage for a much longer period than those of the average hybrid tea rose;

(*h*) Ability or tendency to produce more blooms than its parents and the latters' progenitors;

(*i*) A distinctive sweet fragrance which may be described (due to lack of scientific nomenclature for fragrance) as that coming out of a jar containing freshly picked pink oleander bloom, spicy white carnation and Rosa centifolia bloom of about equal proportion;

(*j*) A distinctive floral pattern (as viewed from above), which may be described as resembling in general form that of the bloom of its relation H. T. "Home Run" (Plant Patent No. 1,537 and issued to this applicant in 1956), but with radically different outer petals which are indentated irregularly but gracefully;

(*k*) Tendency to grow and bloom better in greenhouses or glass-houses than in outdoor gardens;

(*l*) Great ease in asexual reproduction—easily rooted, budded or grafted.

ASEXUAL REPRODUCTION

The above described characteristics and the combination thereof of this new variety have been found to be established definitely and to hold true through succeeding asexual reproductions. Buddings, graftings, layerages and cuttings, performed in Fairport, N. Y., have always confirmed the fact that said characteristics and the combination thereof are transmissible asexually.

PICTURE OF THE NEW VARIETY

The accompanying picture of this new variety shows the shape, relative size and colors of its various parts as seen in the greenhouse, with daylight coming through the glasses, on a fair day in the month of August, 1957. There are little or no differentiating features in the very young leaves, immature buds and very old blooms, and no special effort has been made to illustrate or color them in detail other than those appearing incidentally in the picture.

In making this picture, I have used the best available oil colors, but due to the very nature of color pigments the colors on this picture may, in time, change like those on any other picture or painting. The correct colors of this new variety's foliage, canes and blooms are the ones described or named specifically in words and numerals, and not the ones that may appear on said picture in future years.

THE COLOR OF THE LIVING TISSUES

The colors of the various parts of this new variety, mentioned in the foregoing and to be described in detail in the pages to follow, are those observed in fair weather in daylight during the early part of August, 1957, in Fairport, N. Y.

The "living" colors of this new variety, like those of any other living plant, are effected by temperature, humidity, soil condition, chemical fertilizers, relative duration of diurnal and nocturnal hours, and other known and unknown factors, and shall undergo appreciable changes from time to time. But the changes in this variety are so slight that each color variation shall remain within its respective general color boundary. The colors specifically named or described in words and numerals in this specification are those seen without glass obstruction in daylight by a person of normal eyesight. Whenever the colors as seen on this new variety in an unobstructed daylight and the colors as seen on it in glass obstructed daylight or in any artificial light do not agree, the colors as seen in unobstructed daylight and described in words and numerals in this specification are the correct colors of this new variety.

The color terminology used in describing the new variety is in accordance to Ridgway's Color Standard and Nomenclature (whenever the plate number followed by the abreviation "Ridg." is given), Horticultural Color Chart of the British Color Council (whenever plate number followed by the abbreviation "Hort." is given), or general meaning of Webster's Dictionary (when plate number is absent). The Ridgway's Color Standard is used when the Horticultural Color Chart does not quite describe the actual specimen, and vice versa.

The place where, and the time when, observations were made for the purpose of compiling data for this specification: Fairport, N. Y., first week in August, 1957.

The following is a detailed description of this new variety of rose plant:

(1) *Parentage*

A seedling originated as a cross of an unnamed pink colored mutant of the known hybrid tea rose "Vierlanden" (seed parent) and an unnamed seedling (pollen parent), the latter being a cross of the known variety "Senator" and a known variety "Florex." The said pollen and seed parents and the varieties "Vierlanden," "Senator" and "Florex" are all hybrid tea roses and not patented.

(2) *Classification*

*Botanic.*—A shrub or woody perennial plant belonging to the continuous or recurrent blooming hybrid variety of the cultivated species of the genus Rosa.

*Commercial.*—A bush type hybrid tea rose plant.

(3) *Plant as a whole*

*Form.*—Bushy and well branched.

*Growth.*—Very vigorous and fast growing.

*Average height at maturity.*—3 feet when grown outdoors as observed in Fairport, N. Y. and 5 or more feet when grown in greenhouse or under glass.

(4) *Canes and stems*

*Very young canes and stems.*—Smooth bark, Oil Green (Plate No. 5 Ridg.) overcast with dull pink.

*Young canes.*—Smooth bark, Peacock Green (Plate No. 6 Ridg.) slightly overcast with light pink.

*Mature or near mature canes.*—Smoother than those of the average hybrid tea, Spinach Green (Plate No. 5 Ridg.)

*Old canes.*—Spinach Green (Plate No. 5 Ridg.) with few brown colored streaks.

(5) *Thorns*

*Size.*—Small, inconspicuous, narrow and pointed slightly downward.

*Distribution and quantity.*—Very small number, averaging less than a dozen to an average size bush, found mostly in the lower half of the bush with practically no thorns on the cutting sections or upper branches.

(6) *Foliages*

*Leaflets.*—Sharp pointed and narrower than those of the average hybrid tea; the length of the average terminal leaflet being always slightly longer than its greatest width; and the length of the average lateral leaflet being one and one-half to twice its greatest width.

*Leaf.*—A compound of three to five leaflets as a general rule.

*Texture.*—Smooth on the obverse or upper side and slightly leatherly on the reverse or under side.

*Serrations.*—Evenly marked but not conspicuous; single form as a general rule.

*Stipules.*—Slightly longer than those of the average hybrid tea rose.

*Color.*—Light Greenish Yellow (Plate No. 5 Ridg.) on both sides, with a light overcast at Oxblood Red (Plate No. 1 Ridg.) when young; Scheele's Green (Plate No. 6 Ridg.) on both surfaces, with the under surface becoming slightly lighter on occasions, when older but before maturity; Spinach Green (Plate No. 5 Ridg.) on the upper side and Lavender Green (Plate No. 000761/1 Hort.) on the under side when mature.

*Quantity.*—About the same as those of Better Times and Briarcliff varieties.

(7) *Flowering bud*

*Size.*—Large.

*Shape.*—Ovoid with a pointed tip when tightly closed; resembling the general form of the capital letter U when one-third to one-half open.

*Color of visible petal when sepals first begin to divide.*—Tyrian Rose (Plate No. 24/3 Hort.).

*Color of visible petals when sepals further divide.*—Tyrian Rose (Plate No 24/3 Hort.).

*Color of visible petals when half blown.*—Tyrian Rose (Plate No. 24/3 Hort) on the outer or under side and Bengal Rose (Plate No. 25/3 Hort.) on the inside or upper side.

*Peduncle.*—Smooth, long and Fern Green (Plate No. 0862/3 Hort.).

*Sepals.*—Slightly serrated, Pea Green (Plate No. 61/2 Hort.) inside, and Agathia Green (Plate No. 60 Hort.) outside.

*Calyx.*—Large, smooth, Agathia Green (Plate No. 60 Hort.) and frequently of a slightly lighter green.

*Opening characteristics.*—Opens up slowly and surely with no tendency to form a "ball"

(8) *Flower*

*Size.*—Two to three inches in diameter when partly opened; four and one-half to five and one-half inches in diameter when almost fully or fully opened.

*Quantity to a stem or flowering branch.*—One as a general rule.

*Form.*—High centered during most of its stages.

*Petalage.*—30 to 40 or more depending upon the seasons.

*Fragrance.*—A distinctive sweet fragrance which may be described as that coming out of a jar containing freshly cut Nerium oleander, spicy white carnation and Rosa centifolia blooms of equal proportion.

*Color of bloom when about one-half to three-fourths opened as viewed from above.*—Bengal Rose (Plate No. 25/3 Hort.).

*Color of bloom when about one-half to three-fourths opened as viewed from below.*—Tyrian Rose (Plate No. 24/3 Hort.), excepting a small area near the calyx; the base of corolla, near the calyx, colored light salmon-yellow and sometimes light cream overcast with light yellow.

*Color of bloom when fully opened but still fresh as viewed from above.*—Rose Bengal (Plate No. 25/3 Hort.), excepting the central area.

*Color of bloom when fully opened but still fresh as viewed from below.*—Tyrian Rose (Plate No. 24/3 Hort.), excepting the basal area.

*General color as viewed from about 25 feet in good daylight during the first two days of bloom.*—Soft, clear, delicate looking medium pink, clearly distinguishable from the pink colorings of Briarcliff, New Dawn, Pink Delight, Abiding Faith, Capistrano, etc., growing nearby.

*General coloring at the end of 5th or 6th day of bloom.*—Light pink with the tip or free end of petals turning pinkish white resembling the complexion of the obverse side of the petal of Baldwin's apple.

*Lasting quality.*—Longer than that of the average hybrid tea rose, and equal to, and often longer than, that of the average hybrid polyantha rose.

(9) *Petals*

*Appearance.*—Satiny on both sides.

*Shape.*—Ovoid (smaller petals); heart shaped with one or more irregular indentations at the free end of each (larger petals).

*Arrangement.*—Partly regular.

*Color.*—Rose Bengal (Plate No. 25/3 Hort.) on the upper surface; Tyrian Rose (Plate No. 24/3 Hort.) on the under surface; a small area of light salmon-yellow, and sometimes light cream overcast with light yellow, on both surfaces of the base section.

*Persistence.*—Drops off cleanly in most temperature and weather conditions.

*Texture.*—Smooth.

*Thickness.*—Medium.

*Veins.*—Clearly visible but not conspicuous.

(10) *Genital organs*

*Stigma.*—Medium in size, Magenta (Plate No. 27/1 Hort.) on the underside and the rim of orifice.

*Style.*—Medium in size, medium in height, light pink with streak of Magenta (Plate No. 27/1 Hort.) or closely related color.

*Pollens.*—Abundant in quantity and Orange Yellow (Plate No. 3 Ridg.) in color.

*Anthers.*—Medium in size, Orange Yellow (Plate No. 3 Ridg.) in color.

*Filaments.*—Uneven in height, Straw Yellow (Plate No. 604/3 Hort.) in color.

*Ovaries.*—All enclosed.

(11) *Hips*

*Size.*—Medium.

*Shape.*—Globular.

*Color when mature.*—Medium orange.

(12) *Cell structure*

*Type.*—Tetraploid.

*Number of chromosomes in somatic cell.*—28.

*Number of chromosomes in germ cell.*—14.

(13) *Blooming habit*

Recurrent or continuous when in good health.

(14) *Quantity of blooms*

Abundant in greenhouse or glass-house culture as observed in Fairport, N. Y.

(15) *Disease resistance and immunity*

No sweeping claim is made as to its capacity or ability to resist black-spots, mildew and other infections common to roses.

I claim:

A new and distinct variety of hybrid tea rose plant classified botanically as, and belonging to, the continuous or recurrent blooming variety of the cultivated species of the genus Rosa, characterized as to novelty by its large and long canes, by its tendency to produce large number of lateral branches, by its narrow and pointed leaflets, by the presence of very few thorns on its lower canes or branches and almost complete absence of thorns from its upper branches or canes, by its tendency to unfurl its petals slowly and to remain in the very desirable partly opened stage longer than the average hybrid tea rose, by its great production of blooms of the quality and size suitable for the cut-flower trade, by its distinctive sweet fragrance, by the clear, clean pink coloring of its bloom, by its distinctive floral pattern, by its tendency to grow better and bloom in greater profusion in glass-houses, and by the combination of all the said characteristics, substantially as described herein and shown in the accompanying picture.

No references cited.